(12) United States Patent
Antich

(10) Patent No.: US 10,986,766 B2
(45) Date of Patent: Apr. 27, 2021

(54) SYSTEM AND RELATED METHODS FOR MONITORING AND ADJUSTING ACTUAL SEED DEPTHS DURING A PLANTING OPERATION BASED ON SOIL MOISTURE CONTENT

(71) Applicant: CNH Industrial America LLC, New Holland, PA (US)

(72) Inventor: Ivan Antich, Willowbrook, IL (US)

(73) Assignee: CNH Industrial America LLC, New Holland, PA (US)

( * ) Notice: Subject to any disclaimer, the term of this patent is extended or adjusted under 35 U.S.C. 154(b) by 152 days.

(21) Appl. No.: 16/152,943

(22) Filed: Oct. 5, 2018

(65) Prior Publication Data
US 2020/0107487 A1   Apr. 9, 2020

(51) Int. Cl.
*A01B 63/16* (2006.01)
*A01C 5/06* (2006.01)
(Continued)

(52) U.S. Cl.
CPC ............ *A01B 63/16* (2013.01); *A01B 63/008* (2013.01); *A01C 5/064* (2013.01); *G01N 33/246* (2013.01);
(Continued)

(58) Field of Classification Search
CPC ....... A01B 63/16; A01B 63/008; A01B 63/14; A01B 63/00; A01B 63/002; A01G 5/064; A01G 5/062; A01G 5/06; A01G 5/00; A01G 1/06; A01G 1/00; A01G 5/068; A01G 5/066; A01G 7/206; A01G 7/20; A01G 7/00; G01N 33/246; G01N 33/24; G01N 33/00; G01N 2033/245
See application file for complete search history.

(56) References Cited

U.S. PATENT DOCUMENTS

| 4,913,070 A | 4/1990 | Morrison, Jr. |
| 6,389,999 B1 | 5/2002 | Duello |
| (Continued) | | |

OTHER PUBLICATIONS

Mark Hanna, *Planter Adjustments for Dry Soil*, Integrated Crop Management, Iowa State University Extension and Outreach, Dated Mar. 22, 2013, 3 pages https://crops.extension.iastate.edu/cropnews/2013/03/planter-adjustments-dry-soil.

(Continued)

*Primary Examiner* — Christopher J. Novosad
(74) *Attorney, Agent, or Firm* — Rebecca L. Henkel; Rickard K. DeMille

(57) ABSTRACT

A method for adjusting a seed depth associated with depositing a seed within a furrow in a field during a planting operation of an agricultural implement determining, by a computing device, a target seed depth based on a moisture content of the soil within the field. The method also includes sensing, by the computing device, a seed depth parameter indicative of a seed depth of the seed relative to a ground surface of the field. The method further includes comparing, by the computing device, the seed depth parameter to a target seed depth parameter that describes the target seed depth. In addition, the method includes initiating, by the computing device, a control action configured to adjust the seed depth parameter towards the target seed depth parameter.

10 Claims, 7 Drawing Sheets

(51) Int. Cl.
*A01B 63/00* (2006.01)
*G01N 33/24* (2006.01)
*A01C 7/20* (2006.01)
*A01C 1/06* (2006.01)

(52) U.S. Cl.
CPC .............. *A01C 1/06* (2013.01); *A01C 5/068* (2013.01); *A01C 7/206* (2013.01); *G01N 2033/245* (2013.01)

(56) References Cited

U.S. PATENT DOCUMENTS

| | | |
|---|---|---|
| 9,167,742 B2 | 10/2015 | Masten et al. |
| 9,307,689 B2 | 4/2016 | Adams et al. |
| 9,516,802 B2 | 12/2016 | Zemenchik |
| 9,629,304 B2 | 4/2017 | Zielke |
| 9,651,536 B1 | 5/2017 | Lund et al. |
| 9,675,004 B2 | 6/2017 | Landphair et al. |
| 9,801,332 B2 | 10/2017 | Landphair et al. |
| 9,864,094 B2 | 1/2018 | Stoller et al. |
| 2016/0037709 A1 | 2/2016 | Sauder et al. |
| 2017/0094894 A1 | 4/2017 | Heim et al. |
| 2018/0116098 A1* | 5/2018 | Bassett .................. A01C 5/04 |

OTHER PUBLICATIONS

John Dietz, *Variable-Depth Planting Controller Coming,* Dated Jan. 25, 2016, 8 pages https://www.agriculture.com/crops/tech-tour/variabledepth-plting-controller-coming_196-ar52031.

*Sense Your Soil, on the Fly,* SmartFirmer, Precision Planting, Precision Seed Spacing Depth Control, 3 pages, retrieved Oct. 5, 2018 http://www.precisionplanting.com/#products/smartfirmer/.

* cited by examiner

SYSTEM AND RELATED METHODS FOR MONITORING AND ADJUSTING ACTUAL SEED DEPTHS DURING A PLANTING OPERATION BASED ON SOIL MOISTURE CONTENT

FIELD

The present disclosure generally relates to planting implements, and more particularly, to systems and methods for monitoring and adjusting an actual seed depth associated with depositing a seed within a furrow during the performance of a planting operation based, at least in part, on soil moisture content.

BACKGROUND

Some planting implements are configured to plant crops by depositing seeds at a desired planting depth during an agricultural operation. For example, planters are generally towed behind a tractor or other work vehicle. Planters generally include a plurality of row units, and each row unit is configured to form a seeding path. Each row unit can include one or more gauge wheels and a ground opening tool. As the implement moves across the field, the ground opening tool opens a furrow, and the row unit deposits seeds into the furrow. The gauge wheel can be positioned a vertical distance relative to the ground opening tool to establish a desired depth of the furrow.

The depth of the furrow can be selected to provide a desired planting depth, which may be selected to enhance crop yield. During such a planting operation, however, seeds may not be consistently placed at the bottom of the furrow. As a result, the actual seed planting depth may be different than the furrow depth. In other words, seeds may be planted shallower than desired (or assumed) based on the furrow depth, which may adversely affect crop yield.

Additionally, moisture content of the soil may affect crop yield. For example, planting seeds in soil that is too wet or too dry can adversely affect crop yield. Moisture content of the soil, however, may vary as the implement is moved through the field.

Accordingly, an improved method and related system for monitoring and adjusting the seed depth associated with depositing a seed within a furrow that addresses one or more of the issues identified above would be welcomed in the technology.

BRIEF DESCRIPTION

Aspects and advantages of the technology will be set forth in part in the following description, or may be obvious from the description, or may be learned through practice of the technology.

In one aspect, the present subject matter is directed to a method for adjusting a seed depth associated with depositing a seed within a furrow in a field during a planting operation of an agricultural implement. The method may include determining, by a computing device, a target seed depth based on a moisture content of the soil within the field; sensing, by the computing device, a seed depth parameter indicative of a seed depth of the seed relative to a ground surface of the field; comparing, by the computing device, the seed depth parameter to a target seed depth parameter that describes the target seed depth; and initiating, by the computing device, a control action configured to adjust the seed depth parameter towards the target seed depth parameter.

In another aspect, the present subject matter is directed to a system for adjusting a seed depth associated with depositing a seed within a furrow in a field during a planting operation of an agricultural implement including a row unit. The system may include a ground engaging tool coupled to a frame of the row unit, and a gauge wheel pivotally coupled to the frame of the row unit. The system may include a seed depth sensor configured to sense a seed depth parameter indicative of a seed depth of the seed relative to a ground surface of the field. The system may include a controller communicatively coupled to the seed depth sensor. The controller may include a processor and associated memory. The memory may store instructions that, when executed by the processor, configure the controller to perform operations. The operations may include determining a target seed depth based on a moisture content of the soil within the field; sensing the seed depth parameter; comparing the seed depth parameter to a target seed depth parameter that describes the target seed depth, the target seed depth parameter describing a target seed depth, and initiating a control action configured to adjust the seed depth parameter towards the target seed depth parameter.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Figure 1:
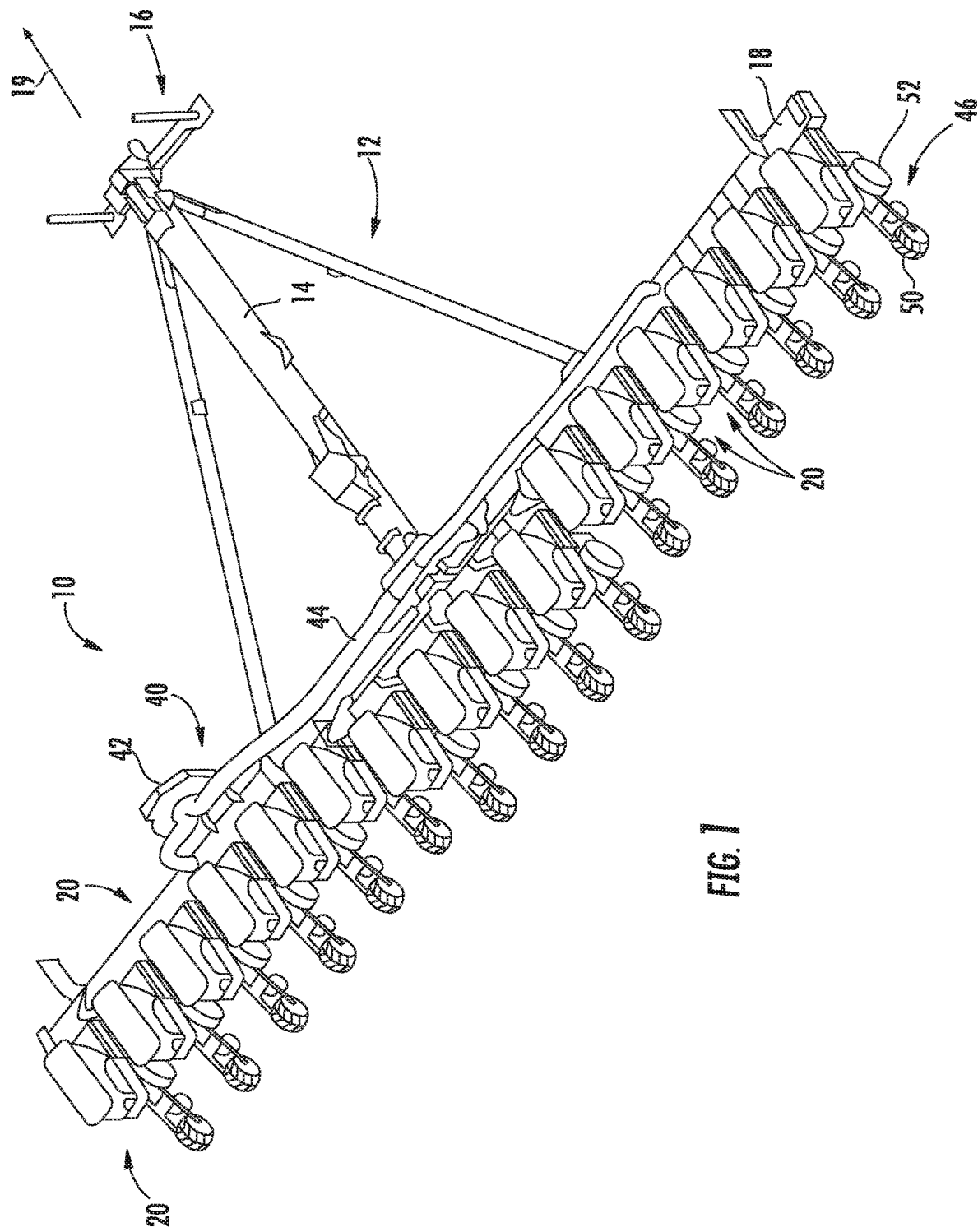
FIG. 1 illustrates a perspective view of one embodiment of an implement according to aspects of the present disclosure.

Repeat use of reference characters in the present specification and drawings is intended to represent the same or analogous features or elements of the present technology.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and related methods for monitoring and adjusting a seed depth associated with depositing a seed within a furrow in a field during a planting operation of an agricultural implement. The agricultural implement may be configured to form a furrow in the field and deposit the seed in the furrow. The seed may be difficult to consistently place in the lowest part or bottom of the furrow. As a result, the actual seed depth may differ from a depth of the furrow.

A seed depth parameter may be sensed that is indicative of the seed depth of the seed within the furrow. The seed depth may be defined relative to the ground surface of the field. The seed depth parameter may be compared to a target seed depth parameter, which may describe a target seed depth. A control action may be initiated to adjust the seed depth parameter towards the target seed depth parameter. In other words, the control action may be configured to adjust the furrow depth in a manner that compensates for the seed being misplaced within the furrow relative to a target location for the seed. For example, the control action may be initiated when it is detected that the seed depth is not equal to a target planting depth associated with the furrow depth. In such an instance, the control action may include adjusting (e.g., increasing) the depth of the furrow to compensate for the location of the seed within the furrow.

Additionally, crop yield may depend on a moisture content of the soil in which the seeds are planted. Generally, soil below the ground surface contains more moisture than soil at the ground surface. More specifically, soil moisture often exhibits a positive correlation with a distance below the ground surface (e.g., seed depth). According to aspects of the present disclosure, the seed depth may be adjusted to compensate for soil moisture, (e.g., such that the seeds may be planted in soil having an appropriate or optimal moisture level for maximizing crop yield). As an example, when planting in wet soil, crop yield may be improved by reducing the seed depth such that the seeds are planted in relatively drier soil. Similarly, when planting in dry soil, crop yield may be improved by increasing seed depth such that the seeds are planted in relatively wetter soil.

More specifically, in some embodiments, the target seed depth may be determined based on a moisture content of the soil within the field. The moisture content of the soil may be actively sensed while the implement is moved across the field. A nominal target seed depth may be established that is associated with a nominal moisture soil content, such as an average or expected soil content of the soil. A moisture depth correction distance may be defined with respect to the nominal target seed depth and may compensate for the soil being drier or wetter than expected. The moisture depth correction distance may be calculated, at least partially, based on the moisture content of the soil. The target seed depth may be proportional (e.g., equal) to the sum of the nominal target seed depth and the moisture depth correction distance. As a result, the target seed depth may be adjusted in response to changes in the moisture depth correction distance (e.g., to compensate for varying soil moisture within the field).

FIG. 1 illustrates a perspective view of an agricultural implement 10. The agricultural implement 10 may generally be configured to be pulled by a work vehicle, such as a tractor. It should be appreciated that, although the implement 10 illustrated herein corresponds to a planter, the implement 10 may generally correspond to any suitable equipment or implement, such as a seeder (e.g., seed disk drill, seed hoe drill) or another seed dispensing implement, a fertilizer dispensing implement, and/or the like.

The implement 10 may have a frame that includes a tow bar assembly 12. The tow bar assembly 12 may include a tow bar 14 and a connection assembly 16. The connection assembly 16 may be disposed at the longitudinally forward end of the tow bar 14 and may be configured to mate with a corresponding hitch of the work vehicle for pulling the implement 10 through a field to perform an agricultural operation, such as a planting or seeding operation. A toolbar 18 may extend generally transverse to a towing direction 19, in which the implement 10 is towed during performance of the agricultural operation. The tow bar 14 may extend generally parallel with the towing direction 19.

The implement 10 may include a plurality of seed planting row units 20 configured to plant seeds in the soil over which the implement is moved. The row units 20 may be connected to the toolbar 18 and may be generally evenly spaced apart in a direction perpendicular to the towing direction 19. Any suitable number of row units 20 may be connected to the toolbar 18. For example, 16 row units are connected with the toolbar 18 as illustrated. However, it should be understood that the implement 10 may include greater or fewer row units 20.

Figure 2:
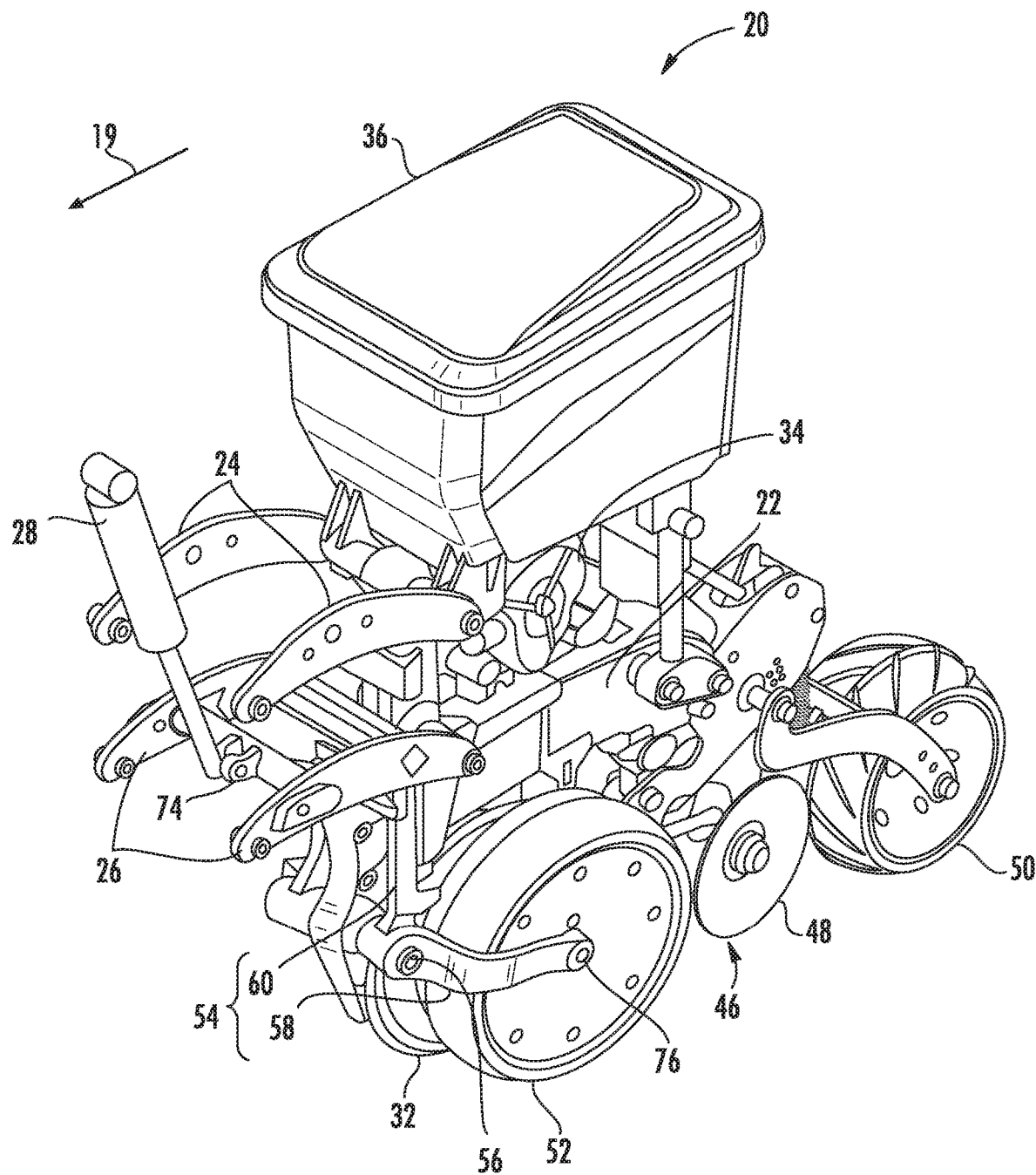
FIG. 2 illustrates an enlarged, partial perspective view of one embodiment of a row unit of the implement shown in FIG. 1 according to aspects of the present disclosure.

Referring to FIG. 2. each row unit 20 may include a frame 22. The frame 22 may be connected to the toolbar 18 (illustrated in FIG. 1). The row unit 20 may include a pair of upper arms 24 and a pair of lower arms 26. The arms 24, 26 may be connected in a parallel configuration to the frame 22 and the toolbar 18 (illustrated in FIG. 1) such that the relative vertical position of the row unit 20 with respect to the toolbar 18 may be adjusted. For example, referring to FIG. 3, in some embodiments the arms 24, 26 may be coupled with a toolbar mount 27 that is mounted to the toolbar 18.

Referring again to FIG, 2, a down force actuator 28 may be configured to apply the down force to the row unit 20. For example, the down force actuator 28 may be connected between the lower arms 26 and the toolbar 18 (illustrated in FIG. 1) or a structure attached to the toolbar 18 (e.g., the toolbar mount 27) such that the down force applied to the row unit 20 may he adjusted by actuating the down force actuator 28. For example, extending the down force actuator 28 may increase the down force, and retracting the down force actuator 28 may decrease the down force. It should be understood that the down force actuator 28 may be connected in any suitable configuration with the row unit 20 for adjusting the down force applied to the row unit 20.

The down force actuator 28 may be selected from a variety of suitable types of actuators. For example, in some embodiments, the down force actuator 28 may be or include a hydraulic actuator, pneumatic actuator, or electro-mechanical actuator.

Figure 3:
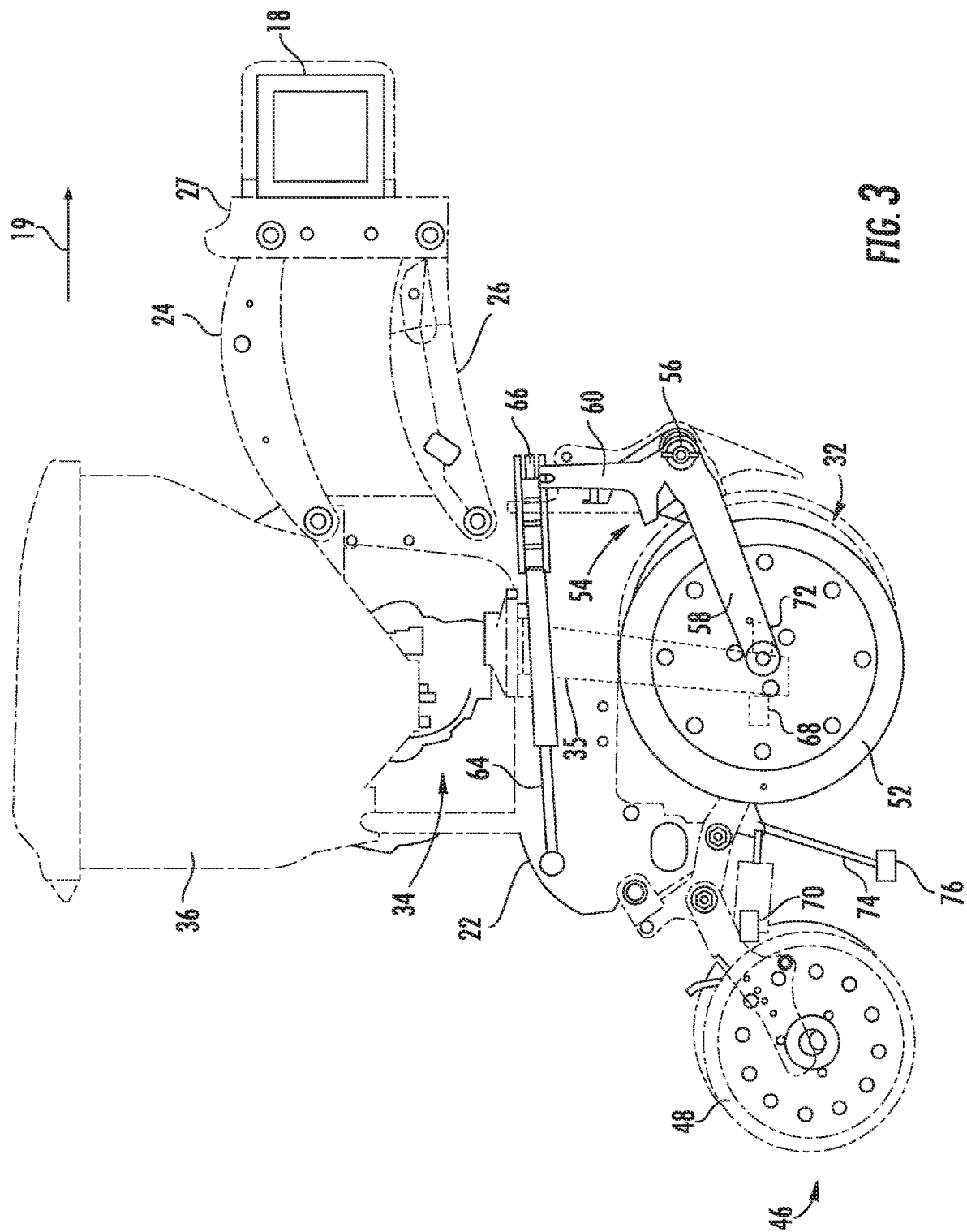
FIG. 3 illustrates a simplified side elevation view of the row unit of FIG. 2 in which portions are omitted or transparent to depict particular components.

FIG. 3 illustrates a simplified side elevation view of the row unit 20 in which portions are omitted or transparent to depict particular components. Referring to FIGS. 2 and 3, during a planting operation, each row unit 20 may form a seed furrow, deposit approximately equally spaced seeds in the seed furrow, and close the seed furrow over the deposited seeds. Each row unit 20 may include a pair of opening discs 32. The opening discs 32 may converge forwardly and downwardly to open the furrow, or trench, as the planting implement 10 moves forward. A seed metering system 34 may receive seeds from a seed hopper 36 and provide individual seeds at a controlled rate for deposit in the bottom of the seed furrow. A vacuum system 40 (illustrated in FIG. 1) may include a fan 42 and air lines 44. The vacuum system 40 may provide vacuum to the seed metering system 34 to facilitate operation of the seed metering system 34. More specifically, the seed metering system 34 may control a flow of the seeds into the furrow through a seed tube 35 (illustrated in FIG. 3).

The row unit 20 may include a seed furrow closing mechanism 46 configured to close the seed furrow after the seeds have been deposited in the seed furrow. The seed furrow closing mechanism 46 may include a pair of pinch wheels or closing discs 48 arranged on opposite sides of the seed furrow and configured to move soil back into the seed furrow and over the seeds deposited in the bottom of the seed furrow. A trailing press wheel 50 (omitted from FIG. 3) may travel along the top of the closed seed furrow and firm the soil replaced in the seed furrow.

A depth to which opening discs 32 are allowed to penetrate the ground (and the resulting depth of the furrow formed by the opening discs 32) may be controlled by a pair of gauge wheels 52. The gauge wheels 52 may be disposed on each side of the opening disc 32. Each gauge wheel 52 may be rotatable mounted to a gauge wheel linkage 54 that is pivotally connected at a pivotal attachment 56 to the seed planting unit frame 22. Each gauge wheel linkage 54 may include a wheel retention arm 58 extending generally rearward from pivotal attachment 56 and a control arm 60 extending generally upward from the pivotal attachment 56. Pivoting the gauge wheel linkage 54 about the pivotal attachment 56 adjusts the position of the gauge wheel 52 relative to the opening discs 32 to adjust the depth of the furrow formed by the opening discs 32.

The control arm 60 of the gauge wheel linkage 54 may be coupled with a gauge wheel actuator 64 by a wobble bracket 66. The gauge wheel actuator 64 may also be coupled with the frame 22 of the row unit 20. The gauge wheel actuator 64 may be configured to adjust a position of the gauge wheel 52 relative to the ground engaging tool(s) (e.g., opening disc(s) 32). For example, the gauge wheel actuator 64 may be extended to raise the gauge wheel 52 relative to the opening disc(s) 32 and thereby increase the depth of the furrow created by the opening discs(s) 32. Similarly, the gauge wheel actuator 64 may be retracted to lower the gauge wheel 52 relative to the opening disc(s) 32 and thereby decrease the depth of the furrow created by the opening discs(s) 32.

A variety of sensors may be disposed on or adjacent the row unit 20. In some embodiments, one or more seed depth sensor(s) 68, 70 may be configured to detect a seed depth parameter indicative of a seed depth of the seed relative to a ground surface of the field. The seed depth sensor(s) 68, 70 may correspond to any suitable sensing device(s) configured to detect or capture image data or other vision-based data (e.g., point cloud data) associated with an orientation of the implement 10 relative to the work vehicle 12. For example, the seed depth sensor(s) 68 may include variety of suitable vision-based sensor types, including an image capture device such as a camera (e.g., an RGB, NIR-RGB, or CIR, or other infrared type camera), a LIDAR sensor, a RADAR sensor, stereographic camera(s) having two or more lenses with a separate image sensor for each lens to allow the camera(s) to capture stereographic or three-dimensional images, and/or the like.

In some embodiments, a least one of the seed depth sensor(s) 68, 70 may include a temperature sensor. The temperature sensor may be configured to sense a position of the seed within the furrow by sensing a temperature difference between the seed and an inner surface of the furrow via the temperature sensor. For example, the temperature sensor may be an optical (e.g., infrared) thermometer. The temperature sensor may be configured to generate a heat map of the seed and a portion of the inner surface of the furrow. The seed may be located within the heat map based on the seed being warmer or cooler than the inner surface of the furrow.

In some embodiments, one of the seed depth sensor(s) 68 may be configured to sense the seed depth parameter proximate a seeding location within the furrow where the seed tube 35 is configured to deposit the seed within the furrow. For example, such seed depth sensor 68 may be located proximate (e.g., coupled to) the seed tube 35, for example as illustrated in FIG. 3. Additionally or alternatively, one of the seed depth sensor(s) 70 may be configured to sense the seed depth parameter proximate a closing location within the furrow where a furrow-closing implement (e.g., the closing discs 48) is configured to close the furrow. For example, such seed depth sensor 70 may be located near the closing discs 48 or a structure connected to the closing discs 48.

The seed depth sensor(s) 68, 70 may be configured to sense the seed depth parameter by detecting an absence of the coating at a location of the seed. In some embodiments, a coating dispenser 72 may be configured to deposit (e.g., spray) a coating on at least a portion of the inner surface of the furrow. The coating dispenser 72 may be configured to deposit the coating on the inner surface of the furrow without depositing the coating on the seed. For example, the coating dispenser 72 may be configured to spray the inner surface of the furrow after the furrow is opened but before the seeds are deposited within the furrow.

In some embodiments, the seed depth sensor(s) 68, 70 may be configured to sense the seed depth parameter by detecting a coating on the seed. The coating may be deposited on the seed before the seed is loaded into the seed hopper 36. Alternatively, the coating dispenser 72 may be configured to spray the coating on the seed without depositing any (or a substantial amount) of the coating on the inner surface of the furrow. For example, the coating dispenser 72 may be configured to spray the coating on the seed before the seed is deposited in the furrow, Although the coating dispenser 72 is illustrated proximate the opening discs 32, it should be understood that the coating dispenser 72 may have any suitable location. As one example, the coating dispenser 72 may be located inside or adjacent the seed metering system 34.

The coating may be a liquid, such as a chemical compound that can be detected as described above. For example, the coating may cause the seed and/or furrow to exhibit a change in color, reflectivity, absorptivity, or another visual characteristic. Alternatively, the coating may be applied at a temperature that is different than a temperature of the furrow and/or seed such that a temperature difference between the seed and furrow may be detected (e.g., by the temperature sensor described above).

In some embodiments, at least one moisture sensor 76 may be configured to sense the moisture content of the soil, for example as described below with reference to FIG. 8. The moisture sensor 76 may be disposed in a variety of locations relative to the row unit 20. For example, in some embodiments, a probe 74 may be coupled with the row unit 20 and extend downward from the row unit 20. The moisture sensor 76 may be mounted on the probe 74 such that the moisture sensor 76 contacts and/or penetrates the soil during the agricultural operation.

In other embodiments, a non-contact moisture sensor may be mounted on or adjacent the row unit 20 such that the non-contact moisture sensor is configured to be proximate the soil without contacting or penetrating the soil. In such embodiments, the non-contact moisture sensor may be disposed on or adjacent to any suitable part or component of the row unit 20, including for example, the gauge wheel linkage 54, any portion of the row unit frame 22, and/or the toolbar 18. In other embodiments, a. moisture sensor may be mounted on the work vehicle or a structure attached to the work vehicle.

Figure 4A:
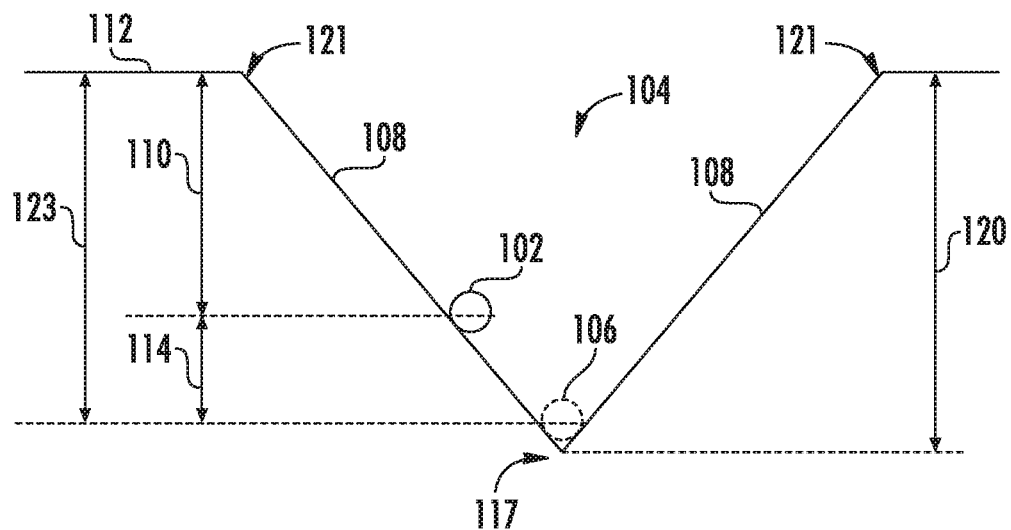
FIG. 4A illustrates a simplified side elevation view of a seed deposited within a furrow and a target seed location within the furrow, according to aspects of the present disclosure.
Figure 4B:
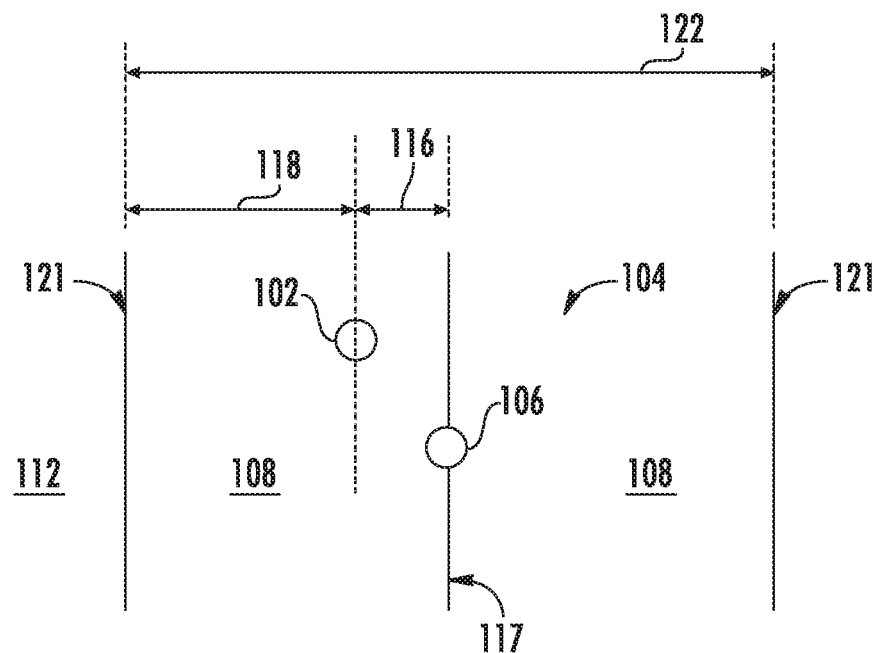
FIG. 4B illustrates a simplified top down view of a seed deposited within a furrow and a target seed location within the furrow according to aspects of the present disclosure.

FIGS. 4A and 4B illustrate simplified side elevation and top down views, respectively, of a seed 102 deposited within a furrow 104 according to aspects of the present disclosure. The furrow 104 may generally have a "V" shape. A target seed location 106 may be defined in the lowest portion of the furrow 104. However, controlling the actual location of the seed 102 may be difficult. For example, the seed 102 may bounce and/or roll when it is deposited in the furrow 104. As a result, the seed 102 may come to rest along a side wall 108 of the furrow 104 in a location other than the target seed location 106, for example as shown in FIGS. 4A and 4B.

Referring to FIG. 4A, a seed depth 110 may be defined as a vertical distance between the location of the seed 102 within the furrow 104 to a ground surface 112 of the field that is adjacent the furrow 104. A depth difference 114 may be defined as a vertical distance between the seed 102 and the target seed location 106, which may be located at the lowest point of the furrow 104.

Referring to FIG. 4B, a seed offset distance 116 may be defined as a horizontal distance between a centerline 117 (e.g., at an intersection of the side walls 108 of the furrow 104) and the location of the seed 102 within the furrow 104. The seed offset distance 116 may be geometrically related to the seed depth 110 (illustrated in FIG. 4A), as one of ordinary skill in the art would understand. For example, various characteristics of the furrow 104 may be estimated or measured that correlate the seed offset distance 116 with the seed depth 110 such that the seed depth 110 may be calculated based on the seed offset distance 116. Example characteristics of the furrow 104 include a slope angle of the side walls 108, a depth 120 of the furrow 104, and width 122 of the furrow 104. The seed offset distance 116 may be visually measured or sensed (e.g., by the visual sensor(s) 68, 70 described above with reference to FIG. 3). The seed depth 110 may be calculated or estimated therefrom.

Similarly, a seed-to-edge distance 118 may be defined as a horizontal distance between the location of the seed 102 and an edge 121 of the furrow 104. The seed-to-edge distance 118 may also be geometrically related with the seed depth 110 based on the various characteristics of the furrow 104 (e.g., the slope angle of the side walls 108) described above such that the seed depth 110 can be calculated based on a measurement of the seed-to-edge distance 118.

The seed-to-edge distance 118 (and other horizontal distances) may be particularly suitable as seed depth parameters. As indicated above, the seed depth sensor(s) 68, 70 may include visual sensors and may be physically located above the furrow 104. As such, the seed depth sensor(s) 68, 70 may be particularly suited for measuring horizontal distances (e.g., the seed-to-edge distance 118). For example, one or more of the seed depth sensor(s) 68, 70 may include a camera or other visual sensor that views the furrow 104 from above as illustrated in FIG. 4B.

A target seed depth parameter may be associated with the target location 106. For example, the target seed depth parameter may be or include at least one of a vertical distance or a horizontal distance that defines the target location 106 relative to the ground surface 112 or a feature of the furrow 104 (e.g., the edge 121 or the centerline 117). For example, the target seed depth parameter may be or include a target seed depth 123, which may be defined as a vertical distance between the ground surface 112 and the target seed location 106. In one embodiment, the target seed depth 123 may be equal to the furrow depth 120. As other examples, the target seed depth parameter may be or include a horizontal distance between the targeted location 106 and at least one of the edge 121 or the centerline 117 of the furrow 104 that describes the target seed depth 123 based on the geometric characteristics of the furrow 104. As indicated above, the target seed location 106 may be defined at a lowest point of the furrow 104, for example at the intersection of the side walls 108 of the furrow 104.

Figure 5:
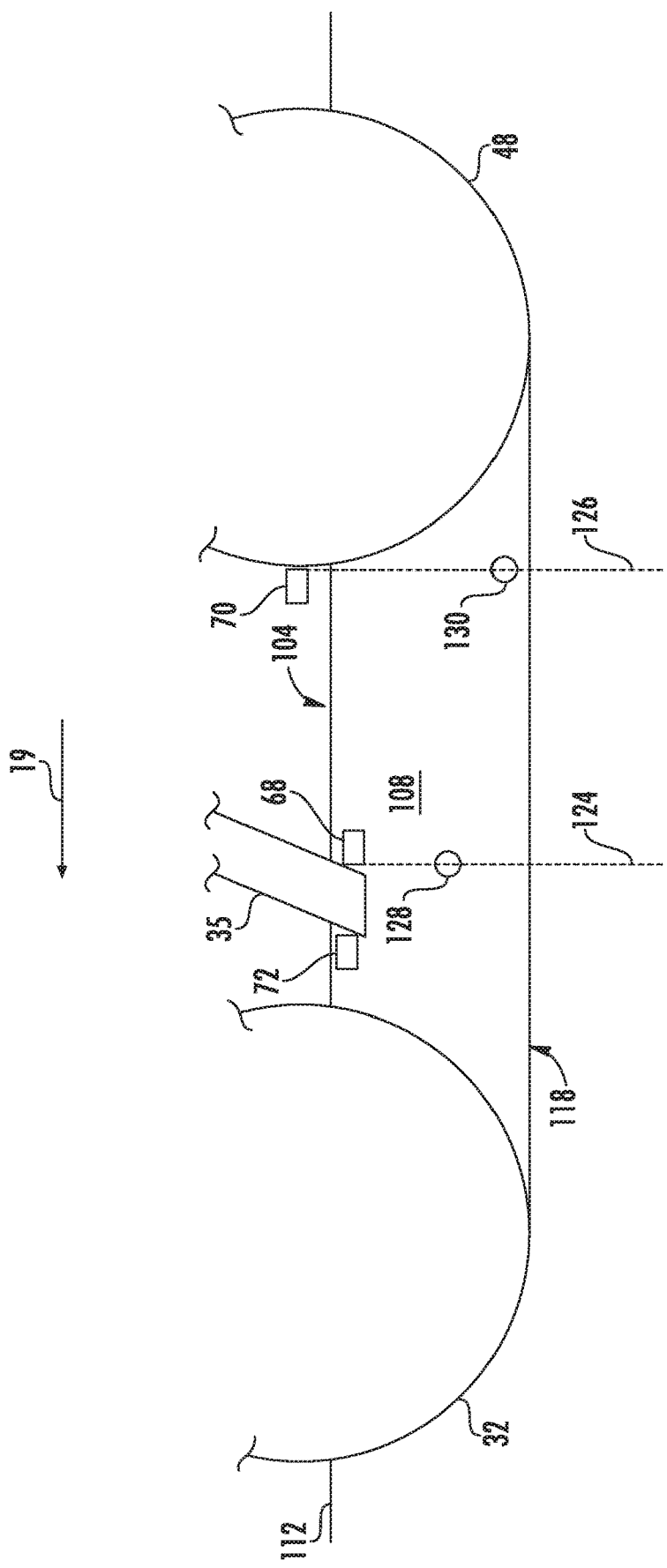
FIG. 5 illustrates a simplified side view of select portions of a row unit of an agricultural implement while depositing seeds within a furrow during performance of a planting operation according to aspects of the present disclosure.

FIG. 5 illustrates a simplified side view of select portions of a row unit of an agricultural implement while depositing seeds within a furrow during the performance of a planting operation according to aspects of the present disclosure. More specifically, the opening disc 32, seed tube 35, and closing disc 48 are schematically illustrated, while other components of the row unit 20 are omitted. The probe 74 and moisture sensor 76 are also omitted from FIG. 5. One seed depth sensor 68 may be configured to sense the seed depth parameter proximate a seeding location 124 within the furrow 104. The seeding location 124 may be defined where the seeds exit the seed tube 35. As one example, the seed depth sensor 68 may be coupled or mounted to the seed tube 35.

Additionally or alternatively, one seed depth sensor(s) 70 may be configured to sense the seed depth parameter proximate a closing location 126, which may be defined where the closing discs 48 close the furrow 104. For example, such seed depth sensor 70 may be located near the closing discs 48 or a structure connected to the closing discs 48.

Seeds deposited by the seed tube 35 may bounce or roll inside the furrow 104. In some embodiments, the sensors may be configured to detect changes in the position of the seed in the furrow 104. For example, a first seed location 128 may be defined at the seeding location 124. A second seed location 130 may be defined at the closing location 126, which may be different than the first seed location 128.

Sensed seed locations (e.g., at the first seed location 128 and/or second seed location 130) may be used to calculate a coefficient of variation (CV) that describes the accuracy of seed spacing. The coefficient of variation can be calculated as a standard deviation of distances between seeds divided by an average distance between seeds. Sensing the location of seeds at multiple locations (e.g., at the first seed location 128 and second seed location 130) within the furrow 104 may provide more accurate CV measurements as compared with sensing the location of the seeds at a single location.

In some embodiments, a speed of the work vehicle and implement 10 may be adjusted (e.g., reduced) in response to CV measurements exceeding a predetermined threshold CV value associated with acceptable seed spacing. For example, the controller 202 may be configured to send an instruction or request to a controller associated with the work vehicle that requests a reduction in a ground speed of the work vehicle. Alternatively, the controller 202 may be configured to provide a notification to the operator (e.g., via the operator interface 212) notifying the operator that the CV measurements have exceeded the predetermined threshold and/or suggesting that the operator reduce the speed of the work vehicle when the CV measurements exceed the predetermined threshold CV value.

It should be understood that a variety of other suitable configurations may be used. As an example, a single seed depth sensor may be employed to collect a single seed depth parameter. In other embodiments, more than two seed depth sensors may be used. Further, the seed depth sensor(s) may be physically located at any suitable location such that the seed depth sensor(s) may detect information about the location of the seed within the furrow 104. For example, in some embodiments, a single seed depth sensor may be include a wide-angle camera that is located such that the wide-angle camera may view a substantial portion of the furrow 104 and may collect information about the depth of the seed at various positions within the furrow 104.

Figure 6:
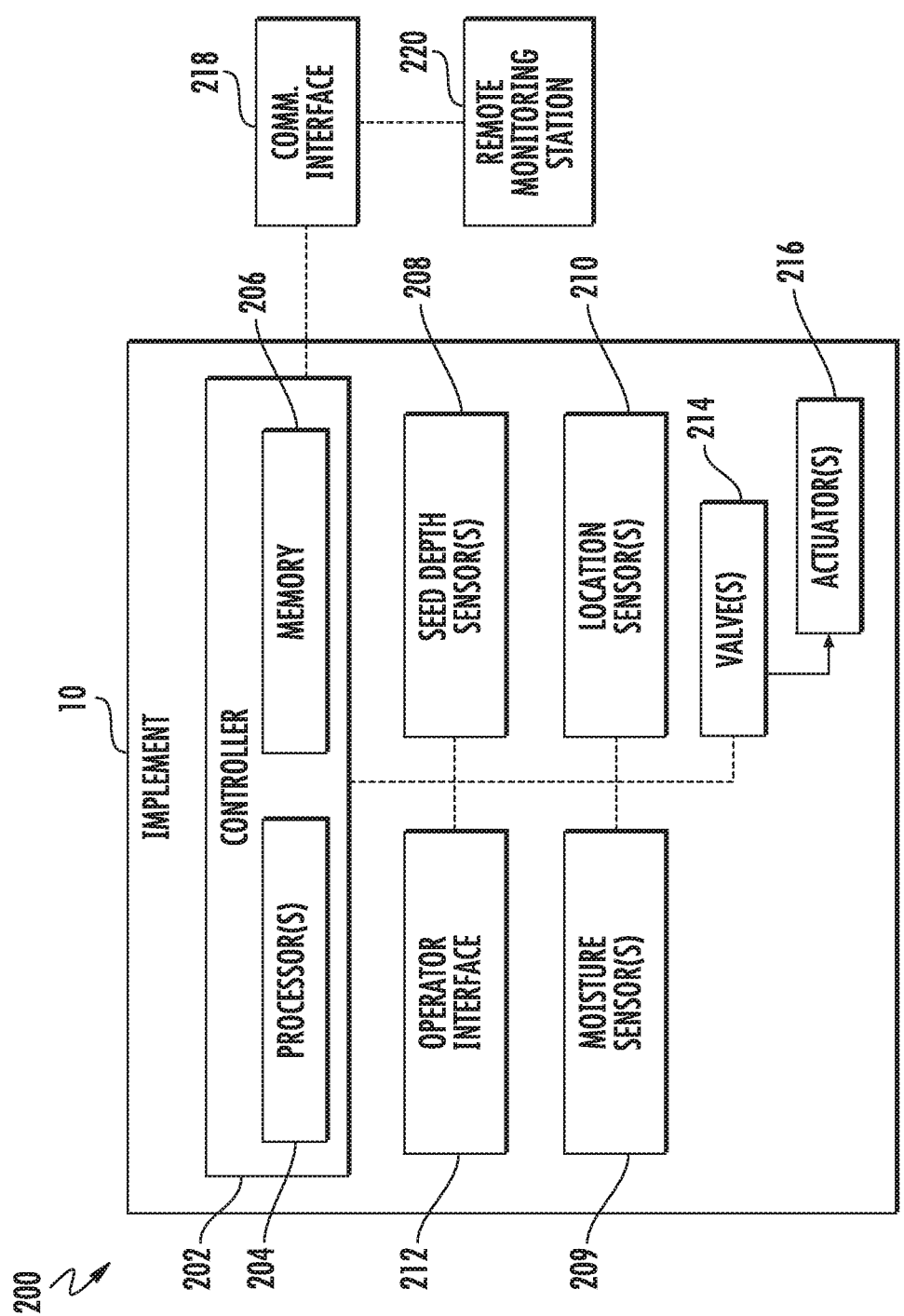
FIG. 6 illustrates a schematic view of one embodiment of a system for adjusting a seed depth associated with depositing a seed within a furrow in a field during a planting operation of an agricultural implement according to aspects of the present disclosure.

Referring to FIG. 6, a schematic view of one embodiment of a system 200 for adjusting a seed depth associated with depositing a seed within a furrow in a field during a planting operation of an agricultural implement is illustrated in accordance with aspects of the present subject matter. In general, the system 200 will be described herein with reference to the implement 10 described above with reference to FIGS. 1 through 5. However, it should be appreciated by those of ordinary skill in the art that the disclosed system 200 may generally be utilized with any implement configured to deposit a particulate into a furrow or trench, such as a seeder (e.g., seed disk drill, seed hoe drill) or another seed dispensing implement, a fertilizer dispensing implement, and/or the like.

The system 200 may generally include at least one controller 202 installed on and/or otherwise provided in operative association with the implement 10 and/or work vehicle. In general, the controller 202 of the disclosed system 200 may correspond to any suitable processor-based device(s), such as a computing device or any combination of computing devices. Thus, in several embodiments, the controller 202 may include one or more processor(s) 204 and associated memory device(s) 206 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory, device(s) 206 of the controller 202 may generally comprise memory element(s) including, but not limited to, computer readable medium (e.g., random access memory (RAM)), computer readable non-volatile medium (e.g., a flash memory), a compact disc-read only memory (CD-ROM), a magneto-optical disk (MOD), a digital versatile disc (DVD) and/or other suitable memory elements. Such memory device(s) 206 may generally be configured to store suitable computer-readable instructions that, when implemented by the processor(s) 204 configure the controller 202 to perform various computer-implemented functions, such as one or more aspects of a method 300 for adjusting a seed depth associated with depositing a seed within a furrow in a field during a planting operation of an agricultural implement as described below with reference to FIG. 7.

It should be appreciated that the controller 202 may correspond to an existing controller of a work vehicle that is configured to pull the implement 10 and/or a controller on the implement 10 itself. Alternatively, the controller 202 may form all or part of a separate plug-in module that may be installed in association with the work vehicle and/or the implement 10 to allow for the disclosed systems and methods to be implemented without requiring additional software to be uploaded onto existing control devices of the work vehicle or implement 10. In addition, the controller 202 may also include various other suitable components, such as a communications circuit or module, a network interface, one or more input/output channels, a data/control bus and/or the like, to allow the controller 202 to be communicatively coupled with any of the various other system components described herein.

The system 200 may include at least one seed depth sensor(s) 208 configured to sense a seed depth parameter that is indicative of a seed depth of a seed relative to a ground surface of the field. The seed depth sensor(s) 208 may correspond to one or more of the seed depth sensor(s) 68, 70 described above with reference to FIGS. 2 through 5.

In some embodiments, the system 200 may also be configured to determine a moisture content of the soil within the field. For example, in some embodiments the system 200 may include at least one moisture sensor 209. The moisture sensor(s) 209 may correspond to the moisture sensor(s) 76 described above with reference to FIG. 3. The moisture sensor(s) 209 may be configured to detect a parameter indicative of the moisture content of the soil. For example, the moisture sensor(s) 209 may be configured to measure an electrical characteristic, such as the electrical conductivity, resistivity, impedance, and/or dielectric permittivity, of the soil. in some embodiments, the moisture sensor 209 may be configured to measure the moisture content by detecting light (e.g., infrared, near-infra-red light, etc.) emitted by the moisture senor 209, or a separate device, and at least partially reflected by the soil The controller 202 may then be configured to determine or estimate the moisture content of the soil based on the measurement signals received from the moisture sensor(s) 209. For instance, the controller 202 may employ a look-up table or suitable mathematical formula stored within its memory 206 that correlates the sensor measurements to the moisture content of the soil.

In some embodiments, the system 200 may include one or more location sensor(s) 210 configured to detect a parameter associated with a geographical or physical location of the implement 10 within the field. For example, in one embodiment, the location sensor(s) 210 may correspond to a GPS receiver configured to detect the GPS coordinates of the implement 10.

In some embodiments, the system 200 may be configured to determine the moisture content of the soil within the field by referencing a moisture map to determine the moisture content for the soil located relative to a current location of the implement 10 within the field. The moisture map may include the moisture content of the soil at a plurality of locations within the field. For example, the controller 202 may determine the current location of the implement using the location sensor(s) 210 and then reference the moisture map to determine the moisture content of the soil proximate the implement.

The controller 202 may be communicatively coupled to an operator interface 212 of the work vehicle 10. In general, the operator interface 212 may correspond to any suitable input device(s) configured to allow the operator to provide operator inputs to the vehicle controller 202, such as a touch screen display, a keyboard, joystick, buttons, knobs, switches, and/or combinations thereof located within a cab of the work vehicle 10. The operator may provide various inputs into the system 200 via the operator interface 212. For example, the operator may input a target seed depth via the operator interface 212 or other parameter associated with performing the control action (e.g., the predetermined threshold described below with reference to FIG. 7).

The controller 202 may be configured to initiate a control action that adjusts the seed depth parameter towards the target seed depth parameter. The controller 202 may adjust a position of the gauge wheel 52 relative to the ground engaging tool(s) (e.g., opening disc(s) 32) to adjust the depth of the furrow formed by the opening disc 32. For example, the controller 202 may be communicatively coupled to one or more control valve(s) 209 configured to regulate the supply of fluid (e.g., hydraulic fluid or air) to one or more corresponding actuator(s) 216. Alternatively, the controller 202 may be configured to regulate a current and/or voltage supply to an electric motor to control the actuator(s) 216, which may include electro-mechanical type actuators. The actuator(s) 216 may correspond to the gauge wheel actuator 64 such that the controller 202 may adjust the position of the gauge wheel 52 relative to the ground engaging tool(s) (e.g., opening disc(s) 32).

In some embodiments, the agricultural implement and/or associated work vehicle may be autonomous or semi-autonomous. In such embodiments, the notification may be provided via a communication interface 218 to a remote monitoring station 220, for example, to a supervisor of the autonomous or semi-autonomous agricultural implement and/or vehicle. The communication interfaces 218 may be configured to wirelessly transmit and/or receive data via any suitable network, such as a local wireless network using any suitable wireless communications protocol (e.g., Wi-Fi, Bluetooth, and/or the like) and/or a broader network, such as a wide-area network (WAN), using any suitable communications protocol (e.g., TCP/IP, HTTP, SMTP, FTP).

Figure 7:
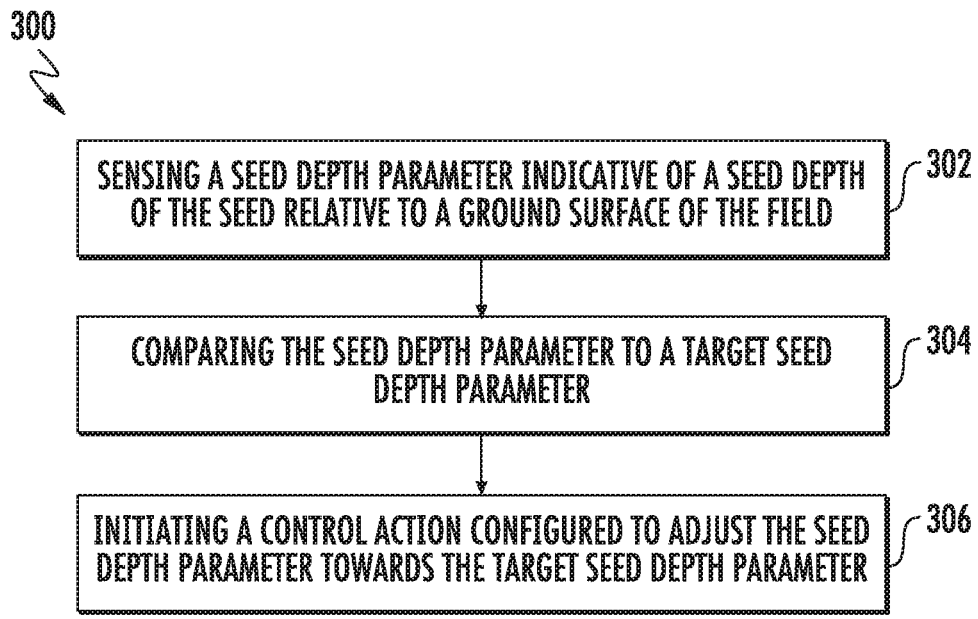
FIG. 7 illustrates a flow diagram of a method for adjusting a seed depth associated with depositing a seed within a furrow in a field during a planting operation of an agricultural implement according to aspects of the present disclosure.

FIG. 7 illustrates a flow diagram of one embodiment of a method 300 for adjusting a seed depth associated with depositing a seed within a furrow in a field during a planting operation of an agricultural implement in accordance with aspects of the present subject matter. Although FIG. 7 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure. Moreover, the method 300 may be described herein with reference to the implement 10 shown in FIG. 1. However, it should be appreciated that the disclosed method 300 may be used to adjust a depth at which any suitable particulate (e.g., seed) or substance (e.g., fertilizer) is deposited within a furrow in a field during an agricultural operation (e.g., a planting operation). The disclosed method 300 may be used with any suitable agricultural implement, such as a seeder (e.g., seed disk drill, seed hoe drill) or another seed dispensing implement, a fertilizer dispensing implement, and/or the like.

At (302), the method 300 may include sensing a seed depth parameter indicative of a seed depth of the seed relative to a ground surface of the field. The seed depth parameter may describe a difference between the seed depth and a depth of the furrow, for example as described above with reference to FIGS. 4A and 4B. Additionally or alternatively, the seed depth parameter may describe a vertical distance between a location of the seed within the furrow and a ground surface of the field, for example as described above with reference to FIGS. 4A and 4B. As examples, the seed depth parameter may include at least one of the seed depth 110, the depth difference 114, the seed offset distance 116, or seed-to-edge distance 118.

The seed depth parameter may be sensed at one or more of a variety of suitable locations. For example, in some embodiments, sensing the seed depth parameter may include sensing the seed depth parameter proximate the seeding location 124 and/or the closing location 126 within the furrow 104, for example as described above with reference to FIG. 5. In some embodiments, the seed depth parameter may be sensed at both the seeding location 124 and the closing location 126. For example, a first seed depth parameter may be sensed at the seeding location 124 and a second seed depth parameter may be sensed at the closing location 126. The first seed depth parameter may be compared with the second seed depth parameter. Such comparison may provide information that can be used to initiate or control a control action at (306), as described below.

In some embodiments, the method 300 may include depositing a coating on the seed and sensing the seed depth parameter by detecting the coating on the seed, for example as described above with reference to FIGS. 3 and 5. Additionally or alternatively, the method 300 may include depositing a coating on at least a portion of the soil, (e.g., an inner surface of the furrow) and detecting an absence of the coating at a location of the seed to sense the seed depth parameter, for example as described above with reference to FIGS. 3 and 5.

In some embodiments, sensing the seed depth parameter may include detecting a temperature difference between the seed and the soil (e.g., an inner surface of the furrow), for example as described above with reference to FIGS. 3 and 5. For example, the seed may be heated or chilled before being deposited within the furrow (e.g., within the seed metering system 34) such that the seed is at a temperature that is higher than a temperature of the inner surface of the furrow.

At (304), the method 300 may include comparing the seed depth parameter to a target seed depth parameter. The target seed depth parameter may include at least one of a vertical distance or a horizontal distance relative to the ground surface 112. More specifically, the target seed depth parameter may be or include the target seed depth 123, for example as described with reference to FIGS. 4A and 4B. Alternatively, the target seed depth parameter may be defined relative to the edge 121 or the centerline 117 of the furrow 104, for example as described with reference to FIGS. 4A and 4B. For instance, in one embodiment, the seed depth parameter may include the seed-to-edge distance 118 described above with reference to FIGS. 4A and 4B. The target seed depth parameter may include a horizontal distance between the edge 121 and the centerline 117 of the furrow that corresponds with the seed being located in the target seed location 106, When the seed-to-edge distance 118 is approximately equal to the distance between the edge 121 and centerline 117, the seed can be determined to be approximately located in the target seed location 106.

In some embodiments, the method 300 may include comparing and/or detecting seed depth parameter measurements. For example, the method 300 may include comparing seed depth parameter measurements at various locations within the furrow 102 (e.g., the seeding location 124 and the closing location 126). As another example, the method 300 may include detecting trends in the seed depth parameter measurement(s) (e.g., increasing, decreasing, etc.). The control action described below may be initiated and/or controlled based on the comparison or trend.

At (306), the method 300 may include initiating a control action configured to adjust the seed depth parameter towards the target seed depth parameter. For example, initiating the control action may include adjusting a position of the gauge wheel 52 of the row unit 20 relative to a ground engaging tool (e.g., the opening disc(s) 32) based on the comparison of the seed depth parameter with the target seed depth parameter. In some embodiments, the control action may be initiated when it is detected that the seed depth is not equal to a target planting depth associated with the furrow depth 120.

In some embodiments, the control action may be initiated when it is detected that the seed depth is not equal to a target planting depth that is associated with the furrow depth. For example, the target planting depth may be approximately equal to the furrow depth. However, when the seed is not deposited in the lowest portion of the furrow, the seed depth may not equal the target planting depth. The control action may be initiated such that a difference between the seed depth and the target planting depth may be reduced.

In some embodiments, the controller 202 may employ a control loop to adjust the seed depth parameter towards the target seed depth parameter. Example control loops include proportional, proportional-integral, and proportional-integral-derivative control loops. Comparing the seed depth parameter to the target seed depth parameter, at (304), may include calculating an error or delta value between the seed depth parameter and the target seed depth parameter. The controller 202 may be configured to employ the control loop to adjust the seed depth parameter towards the target seed depth parameter and minimize the error or delta value.

In some embodiments, comparing the seed depth with the target depth may include detecting when the seed depth is less than the target seed depth by at least a predetermined threshold. The predetermined threshold may be defined as an acceptable deviation from the target seed depth. For example, deviations in the seed depth that are within the predetermined threshold may not substantially adversely affect crop yield, emergence, and/or another metric associated with the growth of the resulting crop. When it is detected that the seed depth is less than the target seed depth by at least the predetermined threshold, the gauge wheel may be raised relative to the ground engaging tool to increase the furrow depth. For example, a control loop may be employed to raise and/or lower the gauge wheel relative to the ground engaging tool to minimize the delta value between the seed depth and the target seed depth.

In some embodiments, the controller 202 may be configured to notify an operator or supervisor of the work vehicle based on the comparison of the seed depth parameter with the target seed depth parameter (e.g., when the seed depth is not equal to the target seed depth). For example, the controller 202 may notify the operator (e.g., via a display screen within the cab or via an audible notification). In other embodiments, the work vehicle and/or implement 10 may be autonomous or semi-autonomous. In such embodiments, the controller 202 may be configured to communicate a notification to a supervisor of the work vehicle and/or implement at the remote monitoring station 220 via the communication interface 218. The supervisor or operator may adjust the position of the gauge wheel 52 to compensate for the seed depth not equaling the target seed depth.

Figure 8:
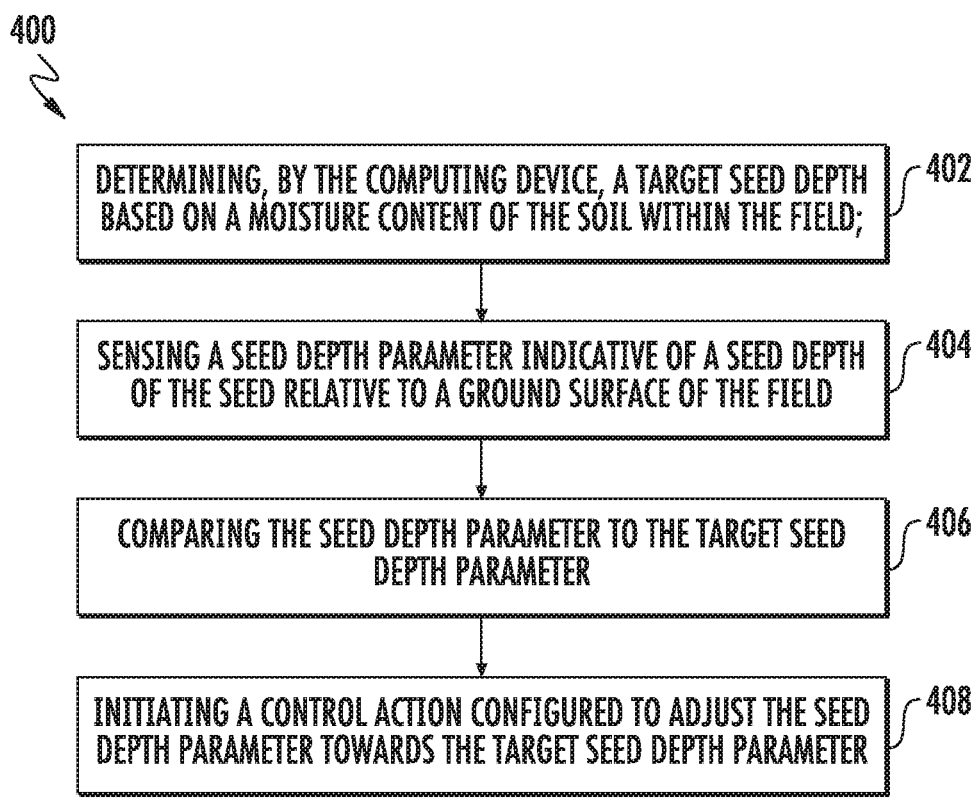
FIG. 8 illustrates a flow diagram of another method for adjusting a seed depth associated with depositing a seed within a furrow in a field during a planting operation of an agricultural implement according to aspects of the present disclosure.

FIG. 8 illustrates a flow diagram of one embodiment of a method 400 for adjusting a seed depth associated with depositing a seed within a furrow in a field during a planting operation of an agricultural implement in accordance with aspects of the present subject matter. Although FIG. 8 depicts steps performed in a particular order for purposes of illustration and discussion, the methods discussed herein are not limited to any particular order or arrangement, One skilled in the art, using the disclosures provided herein, will appreciate that various steps of the methods disclosed herein can be omitted, rearranged, combined, and/or adapted in various ways without deviating from the scope of the present disclosure. Moreover, the method 400 may be described herein with reference to the implement 10 shown in FIG. 1. However, it should be appreciated that the disclosed method 400 may be used to adjust a depth at which any suitable particulate (e.g., seed) or substance (e.g., fertilizer) is deposited within a furrow in a field during an agricultural operation e.g., a planting operation). The disclosed method 400 may be used with any suitable agricultural implement, such as a seeder (e.g., seed disk drill, seed hoe drill) or another seed dispensing implement, a fertilizer dispensing implement, and/or the like.

At (402), the method 400 may include determining the target seed depth based on a moisture content of the soil within the field. As an example, the method 400 may include actively sensing the moisture content of the soil as the implement is moved across the field. The controller 202 may receive signals from one or more moisture sensors 209 configured to sense the moisture content of the soil. The moisture sensor 209 may be configured to measure the electrical conductivity, resistivity, impedance, and/or dielectric permittivity of the soil. In some embodiments, the moisture sensor 209 may be configured to sense light e.g., (infrared or near-infra-red light) reflected by the soil after being emitted by the moisture senor 209, or a separate device.

In some embodiments, the system 200 may be configured to determine the moisture content of the soil within the field by referencing a moisture map to determine the moisture content for the soil located relative to the current location of the implement 10 within the field. For example, the controller 202 may receive signals that are indicative of the location of the implement from the location sensor(s) 210 (e.g., GPS receiver). The controller 202 may reference a moisture map that includes the moisture content of the soil at a plurality of locations within the field.

In other embodiments, the method 400 include performing evapotranspiration and/or drainage modeling based on weather conditions (e.g., temperature, relative humidity, etc.), soil maps, topography, tillage practice, time since the last rainfall, and/or magnitude of the last rainfall, and the like to determine or estimate the moisture content of the soil within the field. In other embodiments, the moisture content may be sensed or determined by one or more remote moisture sensors, such as an array of field based sensors.

Such sensors may wirelessly communicate data describing the moisture content of the soil to the controller 202 of the implement 10.

In some embodiments, determining the target seed depth based on the moisture content of the soil within the field may include establishing a nominal target seed depth and calculating a moisture depth correction distance with respect to the nominal target seed depth based on the moisture content. Establishing the nominal target seed depth may include receiving the nominal target seed depth from the operator of the work vehicle (e.g., as an input via the operator interface 212). As another example, the operator may input one or more characteristics of the planting operation, such as the crop type and/or a soil characteristic. The nominal target seed depth may be calculated based on the input characteristics.

The moisture depth correction distance may be configured to compensate for the moisture content of the soil. As indicated above, crop yield may be improved by increasing the seed depth when planting in dry soil. Similarly, crop yield may be increased by decreasing the seed depth when planning in wet soil. As such, the moisture depth correction may be configured to compensate for the moisture content of the soil compared with a nominal moisture content that corresponds with the nominal target seed depth. The target seed depth may be proportional (e.g., equal) to a sum of the nominal target seed depth and the moisture depth correction distance. Thus, the resulting target seed depth may be adjusted for the moisture content of the soil in which the seeds are being planted.

In some embodiments, determining the target seed depth based on the moisture content of the soil within the field may include updating the target seed depth based on detected changes in the moisture content of the soil. As an example, the target seed depth may be updated as the implement 10 is moved across the field in response to detecting different moisture levels in different areas of the field. For example, the moisture depth correction distance may be periodically updated (e.g., calculated), for example as described above. In some embodiments, the target seed depth may be periodically updated in regular intervals, such as after a predetermined time interval has passed since the last update of the target seed depth. In other embodiments, the target seed depth may be updated only when a newly sensed moisture content exceeds a previously sensed moisture content by at least a predetermined threshold.

At (404), the method 400 may include sensing a seed depth parameter indicative of a seed depth of the seed relative to a ground surface of the field, for example as described above with reference to step (302) of method 300.

At (406), the method 400 may include the method 400 may include comparing the seed depth parameter to the target seed depth parameter that describes the target seed depth, for example as described above with reference to step (304) of method 300.

At (408), the method 400 may include initiating a control action configured to adjust the seed depth parameter towards the target seed depth parameter, for example as described above with reference to step (306) of method 300.

In some embodiments, some of the steps or aspects of method 300 and/or method 400 described herein may be performed remotely, such as at the remote monitoring station 220. For example, the controller 202 may wirelessly communicate the seed depth parameter, target seed depth parameter, the comparison therebetween, and/or the soil moisture to the remote monitoring station 220. A controller at the remote monitoring station 220 may send instructions to initiate the control action based on one or more of the wirelessly communicated signals. For example, the controller at the remote monitoring station 220 may compare the seed depth parameter with the target seed depth parameter and instruct the controller 202 of the implement 10 to initiate the control action. The controller of the remote monitoring station 220 may control one or more aspects of the control action.

It is to be understood that the steps of the method 300 and method 400 may be performed by the controller 202 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 202 described herein, such as the method 300, is implemented in software code or instructions which are tangibly stored on a tangible computer readable medium. The controller 202 loads the software code or instructions via a direct interface with the computer readable medium or via a wired and/or wireless network, Upon loading and executing such software code or instructions by the controller 202, the controller 202 may perform any of the functionality of the controller 202 described herein, including any steps of the method 300 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A method for adjusting a seed depth associated with depositing a seed within a furrow in soil within a field during a planting operation of an agricultural implement, the method comprising:

determining, by a computing device, a target seed depth based on a moisture content of the soil within the field;

sensing, by sensors operatively connected to the computing device, a seed depth parameter indicative of a seed depth of the seed within the furrow relative to a ground surface of the field, wherein sensing the seed depth parameter comprises sensing within the furrow in a first seed location where seed is deposited from a seed tube and sensing the seed depth parameter in a second seed location where seed previously deposited in the furrow is positioned next to a closing location within the furrow;

comparing, by the computing device, the seed depth parameter of seed deposited in the first location with the seed depth parameter of seed in the second location;

determining an average seed depth parameter from a computation of the seed depth parameter in the first location and the seed depth parameter in the second location;

comparing, by the computing device, the average seed depth parameter to a target seed depth parameter that describes the target seed depth; and initiating, by the computing device, a control action configured to adjust the seed depth parameter towards the target seed depth parameter.

2. The method of claim 1, further comprising actively sensing the moisture content of the soil as the agricultural implement is moved across the field.

3. The method of claim 1, wherein determining the target seed depth based on the moisture content of the soil within the field comprises establishing a nominal target seed depth and calculating a moisture depth correction distance with respect to the nominal target seed depth based on the moisture content.

4. The method of claim 3, wherein the target seed depth is proportional to a sum of the nominal target seed depth and a moisture offset distance.

5. The method of claim 1, wherein determining the target seed depth based on the moisture content of the soil within the field comprises updating the target seed depth based on detected changes in the moisture content of the soil.

6. The method of claim 1, wherein initiating the control action comprises adjusting a position of a gauge wheel of a row unit of the agricultural implement relative to a ground engaging tool of the row unit based on the comparison of the seed depth parameter with the target seed depth parameter.

7. The method of claim 6, wherein adjusting a position of the gauge wheel relative to the ground engaging tool comprises, when the comparison of the seed depth parameter with the target seed depth parameter indicates that the seed depth is less than the target seed depth, raising the gauge wheel relative to the ground engaging tool to increase the depth of the furrow.

8. The method of claim 1, wherein the seed depth parameter describes at least one of the following:
a difference between the seed depth and a depth of the furrow; or a vertical distance between a location of the seed within the furrow and a ground surface of the field.

9. The method of claim 1, further comprising sensing the seed depth parameter by detecting a coating on the seed.

10. The method of claim 1, wherein the control action is initiated when a determination is made by the computing device that the seed depth is not equal to a target planting depth associated with the furrow depth.

* * * * *